(12) United States Patent
McCombs et al.

(10) Patent No.: US 6,186,477 B1
(45) Date of Patent: Feb. 13, 2001

(54) GAS BY-PASS VALVE

(75) Inventors: Norman R. McCombs, Tonawanda; Anthony J. Staub, Hamburg, both of NY (US)

(73) Assignee: AirSep Corporation, Buffalo, NY (US)

( * ) Notice: Under 35 U.S.C. 154(b), the term of this patent shall be extended for 0 days.

(21) Appl. No.: 09/305,604

(22) Filed: May 5, 1999

(51) Int. Cl.$^7$ ........................................... F16K 1/32
(52) U.S. Cl. ........................ 251/323; 251/321; 251/900; 128/205.24
(58) Field of Search .................... 251/321, 900, 251/284, 323; 128/204.26, 205.24; 222/402.25

(56) References Cited

U.S. PATENT DOCUMENTS

| | | | |
|---|---|---|---|
| 1,568,159 | * | 1/1926 | Heywood .............................. 251/321 |
| 1,847,281 | * | 3/1932 | Uhri, Jr. .............................. 251/321 |
| 2,514,030 | * | 7/1950 | Coyle et al. ..................... 251/321 X |
| 2,565,050 | * | 8/1951 | Smith .............................. 222/402.25 |
| 2,654,562 | * | 10/1953 | Foster .............................. 251/284 X |
| 2,729,367 | * | 1/1956 | Samuels .......................... 222/402.25 |
| 2,787,280 | * | 4/1957 | Arpin .............................. 128/205.24 |
| 3,221,946 | * | 12/1965 | Riley .............................. 222/402.25 |
| 3,588,040 | * | 6/1971 | Ward .............................. 251/321 X |
| 3,938,555 | * | 2/1976 | Swickley .......................... 251/284 X |
| 4,237,935 | | 12/1980 | Delmonte et al. . |
| 5,065,982 | * | 11/1991 | Shih .............................. 251/321 X |
| 5,364,070 | * | 11/1994 | Crow .............................. 251/323 X |
| 5,460,174 | * | 10/1995 | Chang .......................... 128/205.24 X |
| 5,537,999 | * | 7/1996 | Dearman et al. ........... 128/205.24 X |
| 5,632,298 | * | 5/1997 | Artinian .......................... 137/908 X |
| 5,704,391 | | 1/1998 | McGowan, Jr. et al. . |
| 5,718,571 | | 2/1998 | Rozek . |
| 5,740,835 | | 4/1998 | Murphy . |
| 5,762,103 | | 6/1998 | Gregoire . |

FOREIGN PATENT DOCUMENTS

82289 * 1/1935 (SE) .................................... 251/321

* cited by examiner

Primary Examiner—Kevin Shaver
Assistant Examiner—John Bastianelli
(74) Attorney, Agent, or Firm—Jaeckle Fleischmann & Mugel, LLP

(57) ABSTRACT

A pressurized gas flow controlling microvalve having a casing and cap which together define a valve chamber having gas flow inlet and outlet ports and a plunger positioned within the valve chamber moveable from a closed position sealing the outlet port to an open position permitting gas to flow through the valve, the plunger having mounted thereon an O-ring which provides the seal for the outlet port.

12 Claims, 4 Drawing Sheets

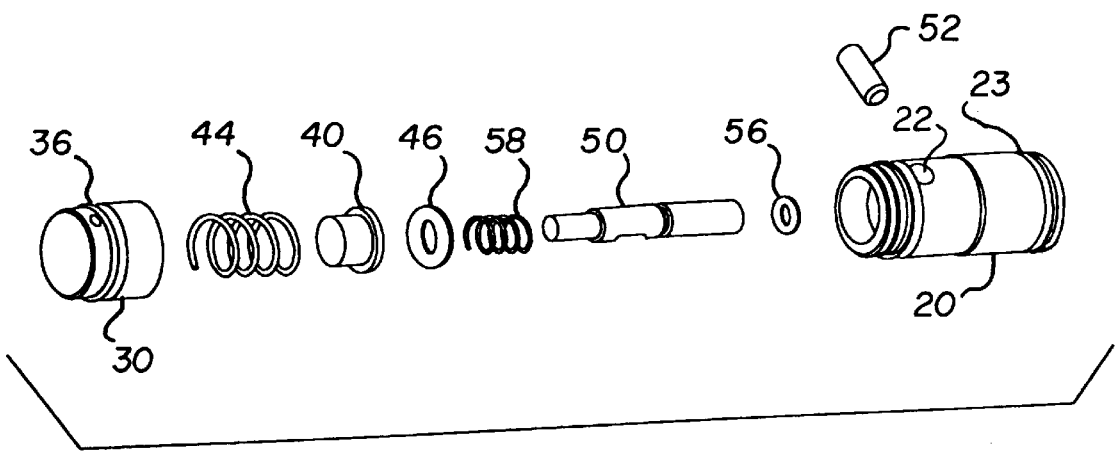
FIG. 2
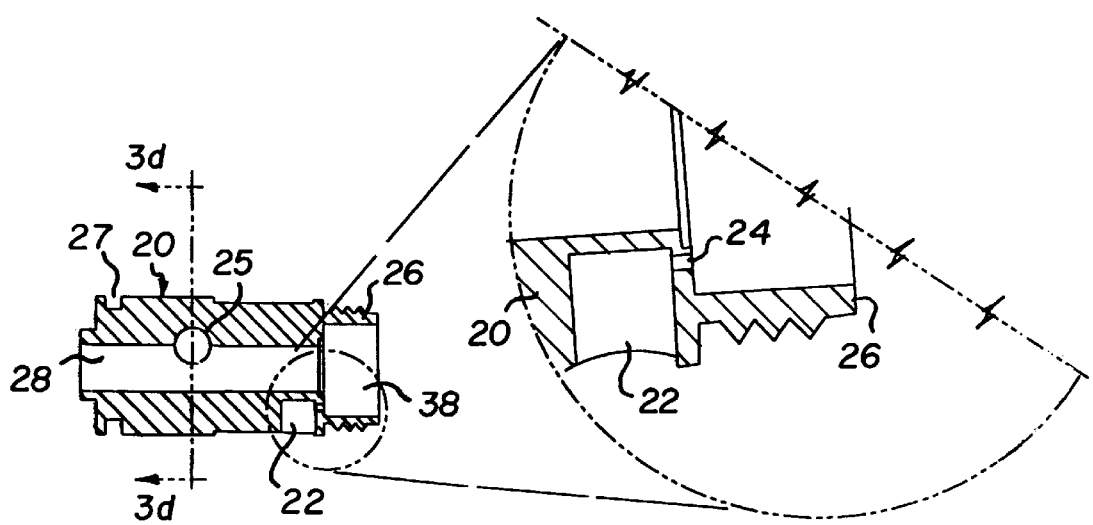
FIG. 3b
FIG. 3c
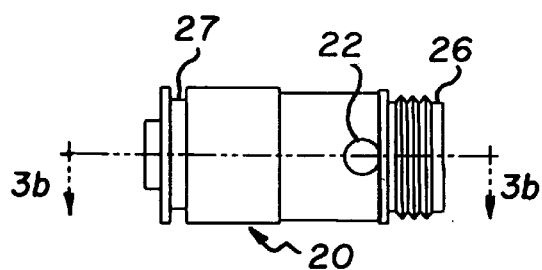
FIG. 3a
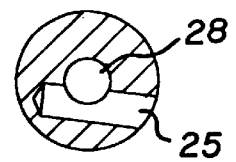
FIG. 3d

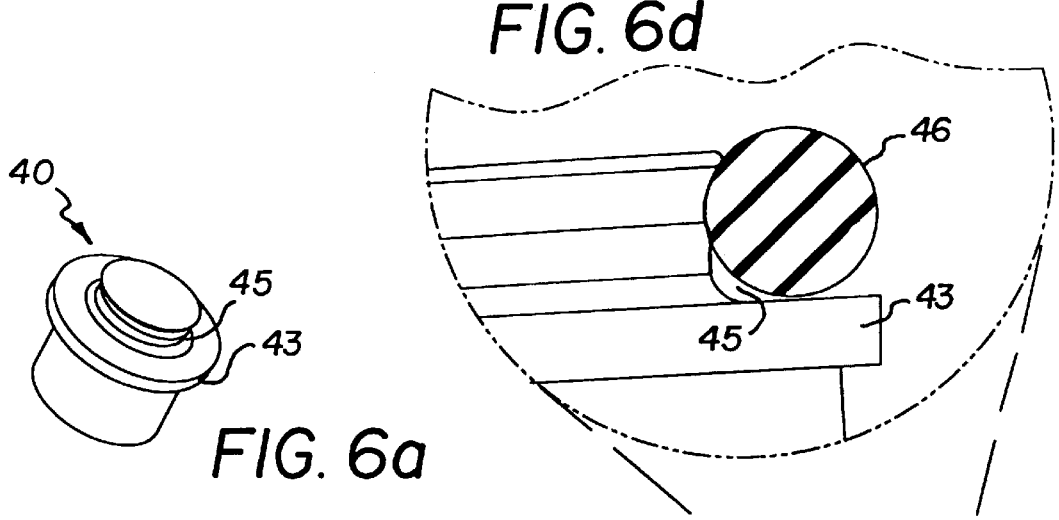
FIG. 6d
FIG. 6a
FIG. 6b
FIG. 6c
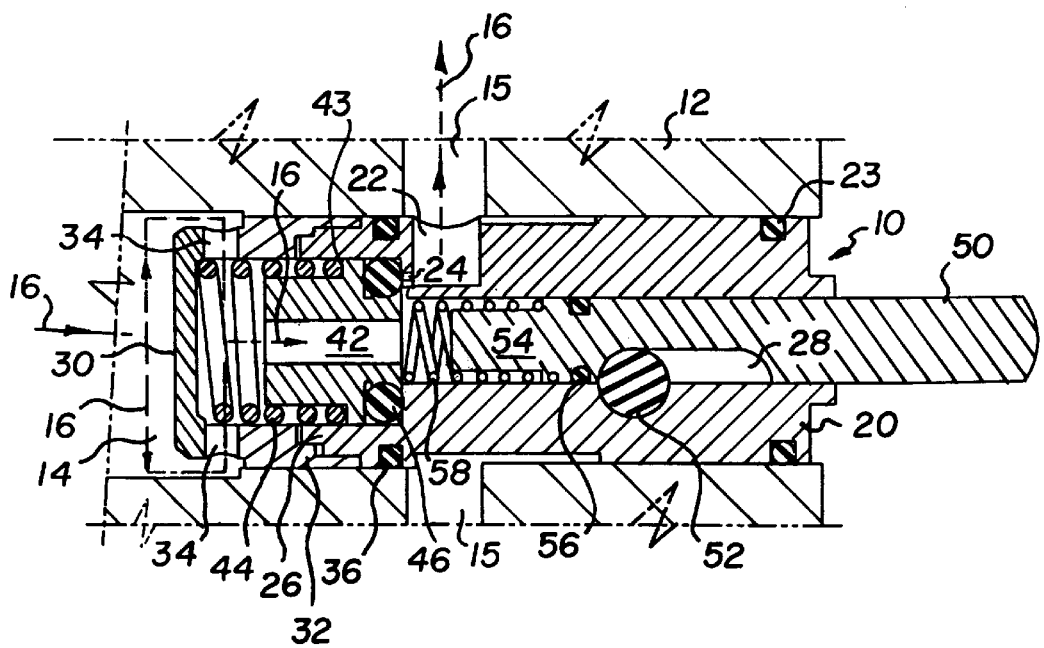
FIG. 7

GAS BY-PASS VALVE

This invention relates to pressurized gas delivery systems and more particularly to a microvalve for controlling the flow of oxygen from a supply source to a user.

BACKGROUND OF INVENTION

It is well known to use gas flow regulators in conjunction with supply sources of gases such as tanks of oxygen containing high pressure oxygen or oxygen gas mixtures, to control both the pressure and the rate of flow of the oxygen or oxygen mixture being released from the tank. More recently, there have been developed separate oxygen control devices that conserve the oxygen supply by limiting its release only during useful times, as for example, only during the inhalation period of the breathing cycle of a patient using the oxygen. Such devices are sensitive to drops in pressure caused by inhalation to activate the oxygen flow only during inhalation.

It also is known to provide in such devices an alternate flow path for the gas mixture or oxygen to be inhaled by the user, as for example a continuous flow by-pass path to be selectively controlled by actuating a valve in the gas flow by-pass path.

Because of the inherent properties of pressurized gases and the need to control carefully their flow rates for human use, we have invented a new microvalve for use in gas flow systems that both is simple in manufacture and will be accurate and reliable in use.

SUMMARY OF THE INVENTION

The present invention comprises a microvalve that may be used in a wide variety of gas flow systems, and conveniently can, but need not, be integral with a gas flow control device. The valve itself contains means such as a casing and cap for defining a valve chamber having gas flow inlet and value seat. Positioned within the valve chamber is a moveable plunger that is held by suitable spring means against the valve seat of the microvalve's outlet port to close the valve seat and prevent gas flow through the outlet port. According to our invention, the valve seat is on an axis displaced from the axis of the valve chamber, and the plunger includes an O-ring, a portion of the leading annular face of which provides the seal against the out let port. To allow the flow of gas through the outlet port, a valve activating stem moves the plunger and O-ring away from the value seat by overcoming the spring means and thereby permitting the gas to flow through the valve.

BRIEF DESCRIPTION OF THE DRAWINGS

The invention as well as its features and advantages will become more apparent from the following description of a preferred embodiment of the invention and the accompanying drawings in which like numerals represent like parts.

FIG. 2 is an exploded view of the parts of the valve of FIGS. 1 a and 1 b;

FIG. 3a is a side view of the valve casing;

FIG. 3b is a cross-sectional view of the valve casing, taken on line 3b —3 b of FIG. 3;

FIG. 3c is an enlarged view of a portion of FIG. 3b;

FIG. 3d is a cross-sectional view of the valve casing, taken on line 3d —3 d of FIG. 3b;

FIGS. 6a, 6b, 6c and 6d are various views of the plunger and the O-ring providing the valve seal; and FIG. 7 is a cross-sectional view of an alternative embodiment of the microvalve.

DETAILED DESCRIPTION OF THE PREFERRED EMBODIMENT

Figure 1A:
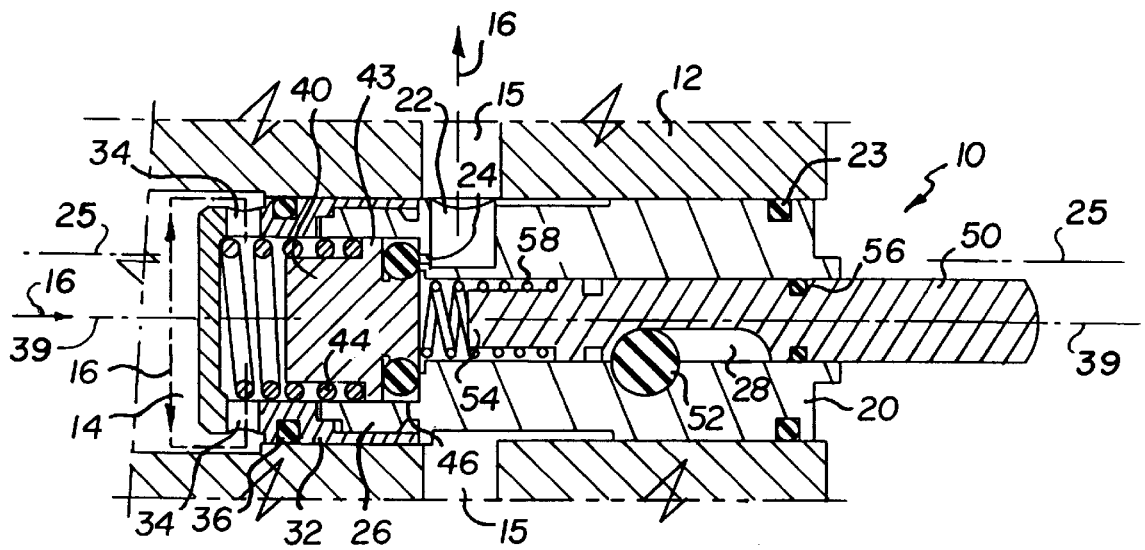
FIG. 1a is a longitudinal cross-sectional view of a microvalve according to the invention in its closed position
Figure 1C:
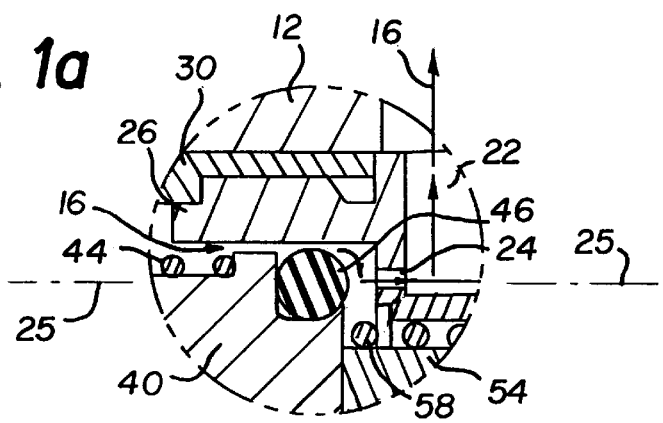
FIG. 1c is an enlarged view of a portion of the valve chamber and plunger in FIG. 1b and partially illustrating the flow path.
Figure 1B:
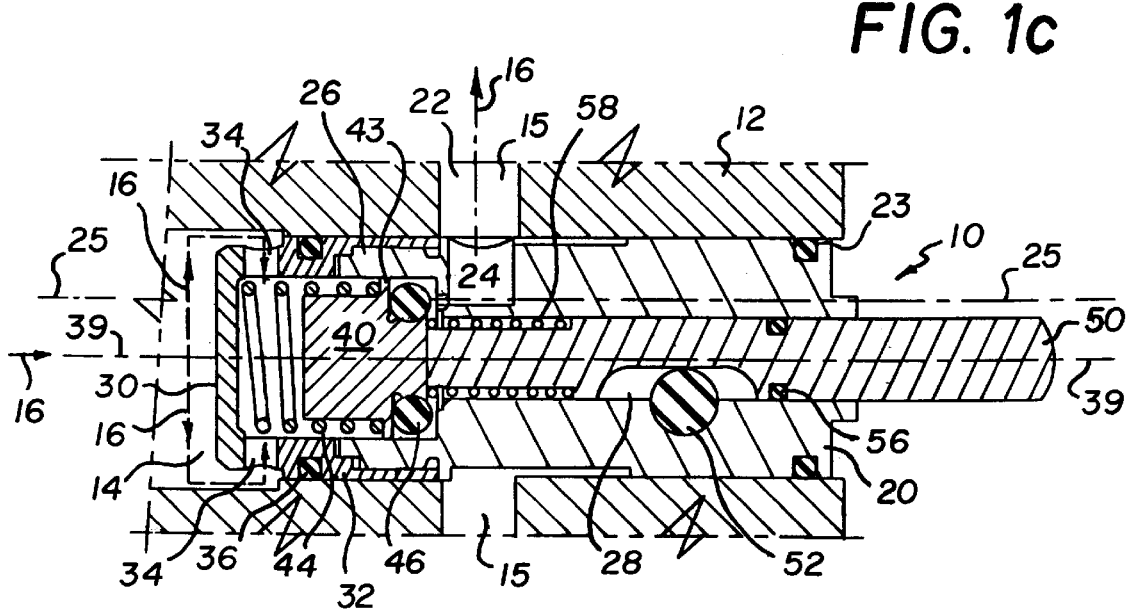
FIG. 1b is a longitudinal cross-sectional view of the microvalve of FIG. 1a in its open position.
Figure 4A:
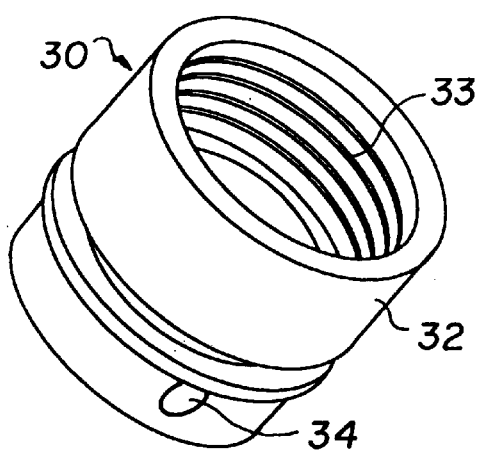
FIG. 4a is a perspective view of the valve cap.
Figure 4B:
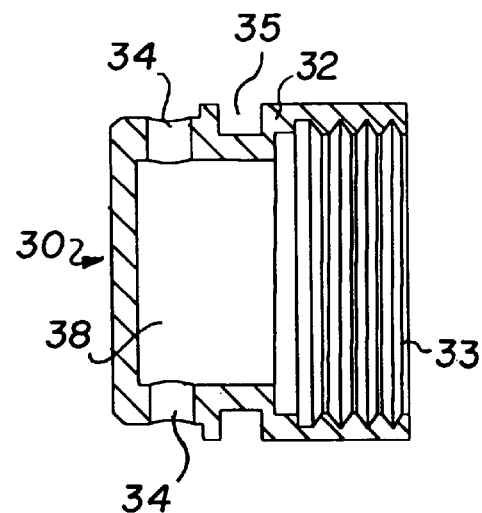
FIG. 4b is a cross-sectional view of the valve cap.
Figure 5A:
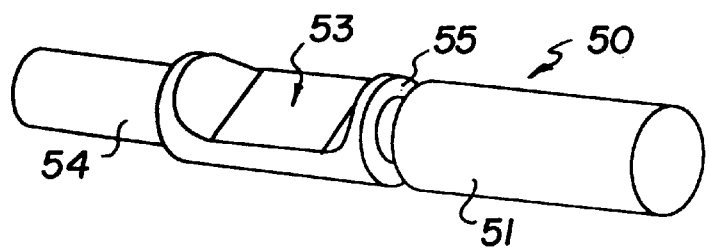
FIGS. 5 a and 5b are views of the valve actuator stem.
Figure 5B:
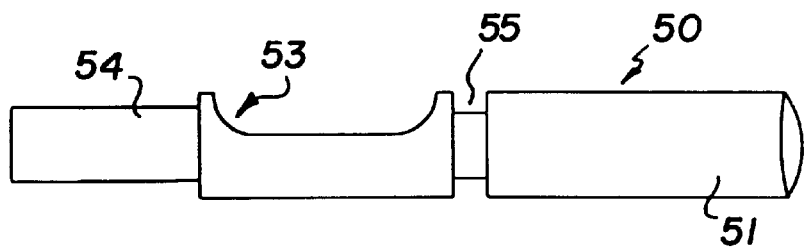

As shown in FIGS. 1a and 1b, microvalve 10, which preferably is generally cylindrical in shape, is mounted in a generally cylindrical cavity 14 of a gas flow control device 12, as for example, the oxygen controller disclosed in Provisional Patent Application No. 60/105,055, filed Oct. 21, 1998. With reference to FIGS. 1a, 1b and 2, the principal components of the microvalve 10 according to our invention include a casing 20, a cap 30, a plunger 40 and a stem 50. When assembled and mounted in cavity 14, valve 10 and device 12 define a gas flow path by which the pressurized gas, such as oxygen or an enriched oxygen mixture from a supply source (not shown) flows in the direction indicated by arrows 16 from cavity 14 to an outlet 15 in device 12 that is in fluid connection to the user of device 12. Outlet 15 of device 12 may be either a single circular opening aligned with an outlet port 22 (e.g., 0.095" diameter) in casing 20, or it may comprise multiple openings 15 either of the same size to facilitate alignment or of different sizes to enable selection from a variety of flow rates. As further shown in FIGS. 1 and 2, valve cap 30 of valve 10 is preferably screw mounted on casing 20 by the threaded extension 33 onto casing extension 26 to form a continuous cylindrical valve chamber 38 (e.g., 0.25" having a longitudinal axis 39 and) in which plunger 40 reciprocates to control the gas flow. Cap 20 contains one or more valve inlet ports 34 (e.g., 0.05" diameter each) for the flow of gas to the valve chamber 38, from which the gas is expelled, when the valve is open, as shown in FIG. 1b, through an accurately dimensioned value seat 24, preferably about 0.014" in diameter, drilled in casing 20 to connect valve chamber 38 with outlet port 22. Valve seat 24 is formed in a shoulder 27 dividing valve chamber 38 from a guide cylinder 28 in casing 20. According to the invention, valve seat 24 is positioned on its own longitudinal axis 25 parallel to and laterally displaced from valve chamber axis 39. As can be seen, valve seat As can be seen, microduct 24 controls the flow rate through valve 10, and inlet port 34 preferably is large enough so as not to impede flow of the gas through value seat 24. To prevent gas leakage around valve 10, suitable static seals such as O-rings 23 and 36 are provided in grooves 27 and 35, reapectively, to seal the outer walls of valve casing 20 and cap 30 to the wall of cavity 14.

A helical compression spring 44 normally biases plunger 40 toward microduct 24 by engagement with a radially extending ring 43 integral with plunger 40. Ring 43 (having e.g., about a 0.245" outer diameter to provide about an overall 0.005" gas flow clearance with valve chamber 38) slidably follows the walls of valve chamber 38 to guide the reciprocating movement of plunger 40 between its valve-open (FIG. 1b) and valve-closed (FIG. 1a) positions. To create the valve seal, plunger 40 is provided with an annular groove 45 shaped generally as shown in FIGS. 6a, 6b and 6c and on the front end of which is mounted an O-ring 46 that acts as the value seal by engagement of a portion of the front annular face of the O-ring with value seat 24. When spring force plunger 40 and O-ring 46 against value seat 24, O-ring 46 is deformed 44 in a predictable, repeatable manner to form at its front annular face an annular flat surface of consistent width sufficient to close value seat 24. As is now apparent, O-ring 46 is able to provide a consistent and reliable seal notwithstanding any rotational motion of plunger 40. To open valve 10 on demand, valve stem 50 is slidably mounted in guide cylinder 28 in casing 20 and includes a valve actuating shaft 54 axially aligned with plunger 40 to open the valve seal by engaging plunger 40 and moving it away from value seat 24. The axial thrust (e.g., about 0.15") of valve stem 50 is delimited by a locking pin 52 that is inserted into a locking hole 25 of casing 20 and engages a notch 53 in valve stem 50, the ends of which notch 53 act as stops for stem 50. Pin 52 may be held in position by various suitable means such as an adhesive or press fitting of pin 52 in hole 25. An O-ring 56 mounted in a groove 55 in stem 50 as shown also provides a gas seal for cylinder 28. To retain stem 50 in its normal extended position, there is provided a helical compression spring 58 one end of which is mounted onto stem shaft 54 and the opposite end of which engages plunger 40. The compressive force of spring 58 is lighter than that of spring 44, such that O-ring 46 does not release its seal of value seat 24 unless valve stem 50 is depressed and shaft 54 engages plunger 40 to open the valve port 22. Actuation of stem 50 by depressing it to open valve 10 may be accomplished by any suitable means (not shown), as by solenoid means in which the external, actuator arm 51 of stem 50 is used as the armature, or by mechanical means in which a manual slide switch mounted on device 12 and having a ramp surface engages arm 51 to cause valve stem 50 to be depressed.

As shown in the alternative embodiment of FIG. 7, plunger 40 at its longitudinal axis 39 alternatively may define a cylindrical gas passageway 42 to enable the pressurized gas to flow through plunger 40 when valve 10 is open and to ease valve opening by equalizing the gas pressure on both ends of plunger 40 when valve 10 is closed. FIG. 7 also illustrates alternative positions for O-ring seals 36 and 56. By relocating O-ring 36 in a groove incasing 20 further assists in preventing leakage at the cap 30/casing 20 interface, whereas the relocated O-ring 56 prevents leakage around locking pin 52.

If valve 10 is used in a by-pass gas flow path for a multifunction oxygen controller, as described in the above identified co-pending provisional application, a user unsatisfied with the amount of oxygen provided by device 12 in its pre-set intermittent mode, may then override the pre-set mode by opening valve 10 and providing oxygen continuously throughout the breathing cycle. The preferred embodiment as described is suitable for controlling the flow of oxygen or an oxygen concentrated gas mixture having a pressure of about 22 psig and a flow rate of about 4 liters per minute, although the valve according to our invention can be designed to work reliably at other pressures within a range from about 10 to about 50 psig and a flow rate within a range from about one to about fifteen liters per minute.

Thus, it can seen that the invention as described contains a number of advantageous features and that various modifications and substitutions may be made to the described embodiment without departing the spirit and scope of the invention as claimed.

What is claimed is:

1. A microvalve for controlling the flow of a pressurized oxygen gas or other gas from a source of the gas to a user, the valve comprising a casing having wall means defining a valve chamber and a guide cylinder longitudinally adjoined along a central longitudinal axis, the valve chamber being larger than the guide cylinder in respective cross sections transverse to the longitudinal axis, the wall means comprising an annular shoulder in the casing at the joinder of the valve chamber and the guide cylinder and transverse to the longitudinal axis, at least one gas inlet port defined by the wall means fluidically connected to the valve chamber and at least one gas outlet port defined by the wall means, the shoulder defining a valve seat on an axis spaced from the central longitudinal axis and fluidically connected to the outlet port, a plunger slidably positioned in the valve chamber and selectively moveable within the valve chamber along the longitudinal axis toward and away from the shoulder, the plunger having a first end transverse to the longitudinal axis and operatively engaging the shoulder in a valve closed position, the plunger comprising means at the first end defining a peripheral groove, and a compressible O-ring defining a front annular surface mounted on the plunger peripheral groove for movement with the plunger between a valve-open position in which the O-ring is spaced from the valve seat to permit gas flow through the valve seat to the outlet port and the valve-closed position in which the front annular surface of the O-ring is compressed against the shoulder with only a portion of the front annular surface engaging the valve seat to close the valve seat and prevent gas flow through the valve seat to the outlet port, means for normally holding the plunger in one of the two positions, and actuating means for moving the plunger to the other of the two positions.

2. The microvalve according to claim 1 in which the plunger is normally held in the closed position and the actuating means moves the plunger to the open position.

3. The microvalve according to claim 1 in which the casing comprises a valve casing part and a valve cap part interconnected to form the valve chamber, and the plunger is slidably mounted in one of the parts.

4. The microvalve according to claim 3 and further comprising first spring means having a spring force for biasing the plunger normally in the closed position, the actuating means comprising a valve stem slidably mounted in the guide cylinder to engage the plunger and move the plunger to the open position by overcoming the spring force, second spring means engaging both the plunger and the valve stem to hold the valve stem out of engagement with the plunger and in a position for actuation, and means for overcoming the second spring means to move the valve stem into engagement with and move the plunger.

5. The microvalve according to claim 4 and further comprising means for limiting the movement of the valve stem.

6. The microvalve according to claim 1 in which the wall means comprises a valve casing and a valve cap interconnected to form the valve chamber, the plunger being mounted within the valve cap and the valve cap defining an inner wall along which the plunger is movable within the valve cap but spaced from the plunger to permit gas to flow around the periphery of the plunger and toward the outlet port.

7. A microvalve for controlling the flow of a pressurized gas comprising a casing defining a valve chamber with a central longitudinal axis, a shoulder formed by the casing and comprising a substantially flat surface area in a plane perpendicular to the longitudinal axis; at least one valve seat formed within the shoulder on an axis spaced from the central longitudinal axis and comprising only a small portion of the surface area of the shoulder; a plunger moveable along the longitudinal axis and comprising a front section operatively engaging the shoulder in a valve closed position, the plunger further comprising a compressible O-ring mounted on the front section of the plunger and having a front annular face engaging and being compressed against the shoulder in which only a portion of the front annular face covers the valve seat in the valve closed position to prevent the flow of gas through the casing.

8. A microvalve according to claim 7 for controlling the flow of a gas from a source having a pressure within a range from about ten to about fifty psig and a flow rate within a range from about one liter per minute to about fifteen liters per minute, and further comprising a gas inlet port defined by the casing to enable the gas to flow into the valve chamber, the valve seat being smaller than the gas inlet port to determine the flow rate through the valve chamber.

9. The microvalve according to claim 7 in which the plunger is normally held in the valve closed position, and further comprising actuating means for moving the plunger to a valve open position in which the O-ring is spaced from the shoulder.

10. The microvalve according to claim 9 in which the casing comprises a valve casing part and a valve cap part interconnected to form the valve chamber, and the plunger is slidably mounted in one of the parts.

11. The microvalve according to claim 9 and further comprising first spring means having a spring force for biasing the plunger normally in the valve closed position, the actuating means comprising a valve stem slidably mounted in the casing to engage the plunger and move the plunger to the valve open position by overcoming the spring force, second spring means engaging both the plunger and the valve stem to hold the valve stem out of engagement with the plunger and in a position for actuation, and means for overcoming the second spring means first to move the valve stem into engagement with the plunger and then to move the plunger to the valve open position.

12. The microvalve according to claim 11 and further comprising means for limiting the movement of the valve stem to define the position of the plunger in the valve open position.

\* \* \* \* \*

UNITED STATES PATENT AND TRADEMARK OFFICE
CERTIFICATE OF CORRECTION

PATENT NO.    : 6,186,477 B1
DATED         : February 13, 2001
INVENTOR(S)   : Norman R. McCombs et al.

It is certified that error appears in the above-identified patent and that said Letters Patent is hereby corrected as shown below:

<u>Title page,</u>
ABSTRACT
Lines 5 and 8, change "outlet port" to -- valve seat --

<u>Column 1,</u>
Lines 37 and 47, change "value" to -- valve --
Line 45, change "out let port" to -- valve seat --

<u>Column 2,</u>
Lines 42 and 52, change "value" to -- valve --
Lines 49 and 50, delete the phrase "As can be seen microduct"
Line 58, change "microduct" to -- valve seat --

<u>Column 3,</u>
Lines 1, 2, 3, 6, 13 and 26, change "value" to -- valve --
Line 2, after "spring" add -- 44 acts to --

Signed and Sealed this

Twenty-third Day of April, 2002

Attest:

Attesting Officer

JAMES E. ROGAN
*Director of the United States Patent and Trademark Office*